(12) United States Patent
Straka et al.

(10) Patent No.: US 10,399,127 B2
(45) Date of Patent: Sep. 3, 2019

(54) PIEZOELECTRIC SYSTEMS AND APPLIANCES FOR REMOVING EYE MAKEUP AND RELATED METHODS

(71) Applicant: L'Oreal, Paris (FR)

(72) Inventors: Scott Straka, Redmond, WA (US); Nicolas Duru, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 69 days.

(21) Appl. No.: 15/639,596

(22) Filed: Jun. 30, 2017

(65) Prior Publication Data

US 2019/0001379 A1 Jan. 3, 2019

(51) Int. Cl.
| | | |
|---|---|---|
| *B08B 3/12* | (2006.01) | |
| *A45D 34/04* | (2006.01) | |
| *A45D 44/00* | (2006.01) | |
| *B06B 1/06* | (2006.01) | |
| *B08B 7/02* | (2006.01) | |
| *A46B 13/02* | (2006.01) | |
| *A61M 35/00* | (2006.01) | |
| *A61F 13/40* | (2006.01) | |

(52) U.S. Cl.
CPC .............. *B08B 3/12* (2013.01); *A45D 34/042* (2013.01); *A45D 44/00* (2013.01); *B06B 1/0603* (2013.01); *B06B 1/0644* (2013.01); *B08B 7/02* (2013.01); *A45D 2200/10* (2013.01); *A45D 2200/1009* (2013.01); *A45D 2200/1063* (2013.01); *A45D 2200/207* (2013.01); *A46B 13/023* (2013.01); *A61M 35/003* (2013.01); *A61M 35/006* (2013.01)

(58) Field of Classification Search
CPC ........... B08B 3/12; B08B 7/02; A45D 34/041; A45D 34/042; A45D 44/00; A45D 2200/10; A45D 2200/109; A45D 2200/1063; A45D 2200/207; B06B 1/0603; B06B 1/0644; A46B 13/023; A61M 35/003; A61M 35/006
USPC .......................................... 401/48, 208, 209
See application file for complete search history.

(56) References Cited

U.S. PATENT DOCUMENTS

| | | | |
|---|---|---|---|
| 4,196,201 A | 4/1980 | Boelle et al. | |
| 2006/0272668 A1* | 12/2006 | Wyatt | A45D 34/04 132/218 |
| 2007/0270748 A1 | 11/2007 | Dacquay et al. | |
| 2008/0138138 A1* | 6/2008 | Gueret | A45D 34/04 401/24 |
| 2010/0054843 A1* | 3/2010 | Howard | A45D 34/04 401/143 |
| 2011/0100866 A1 | 5/2011 | Gueret | |

(Continued)

FOREIGN PATENT DOCUMENTS

| | | |
|---|---|---|
| EP | 2 263 580 A2 | 12/2010 |
| JP | 2016137116 A | 8/2016 |
| WO | 2012013542 A1 | 2/2012 |

OTHER PUBLICATIONS

International Search Report and Written Opinion dated Sep. 14, 2018, issued in corresponding Application No. PCT/US2018/038210 filed Jun. 19, 2018, 29 pages.

*Primary Examiner* — Huyen D Le
(74) *Attorney, Agent, or Firm* — Christensen O'Connor Johnson Kindness PLLC

(57) ABSTRACT

Piezoelectric systems and appliances for removing eye makeup and related methods are described.

17 Claims, 5 Drawing Sheets

(56) References Cited

U.S. PATENT DOCUMENTS

| | | | |
|---|---|---|---|
| 2012/0109041 A1* | 5/2012 | Munz | A45D 34/041 |
| | | | 604/20 |
| 2012/0271222 A1 | 10/2012 | Reed et al. | |
| 2014/0214062 A1 | 7/2014 | Rynerson et al. | |
| 2015/0130325 A1 | 5/2015 | Suenaga | |
| 2015/0182415 A1 | 7/2015 | Olkowski et al. | |
| 2015/0196452 A1* | 7/2015 | Meyer | A45D 34/04 |
| | | | 601/160 |
| 2015/0349241 A1 | 12/2015 | Murakami et al. | |
| 2017/0191918 A1* | 7/2017 | Yan | G01N 11/16 |

\* cited by examiner

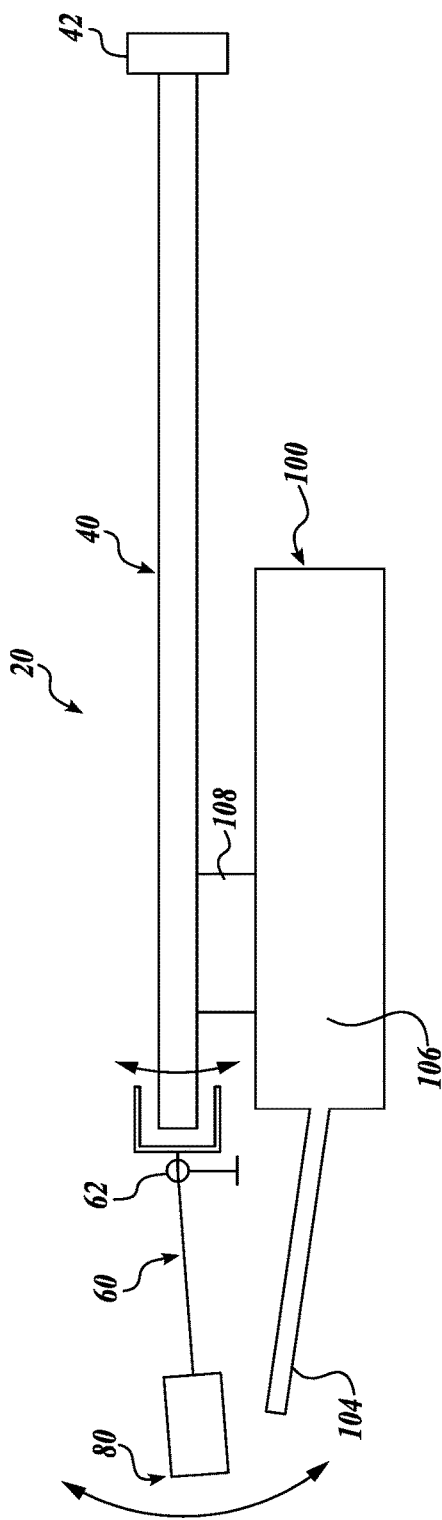
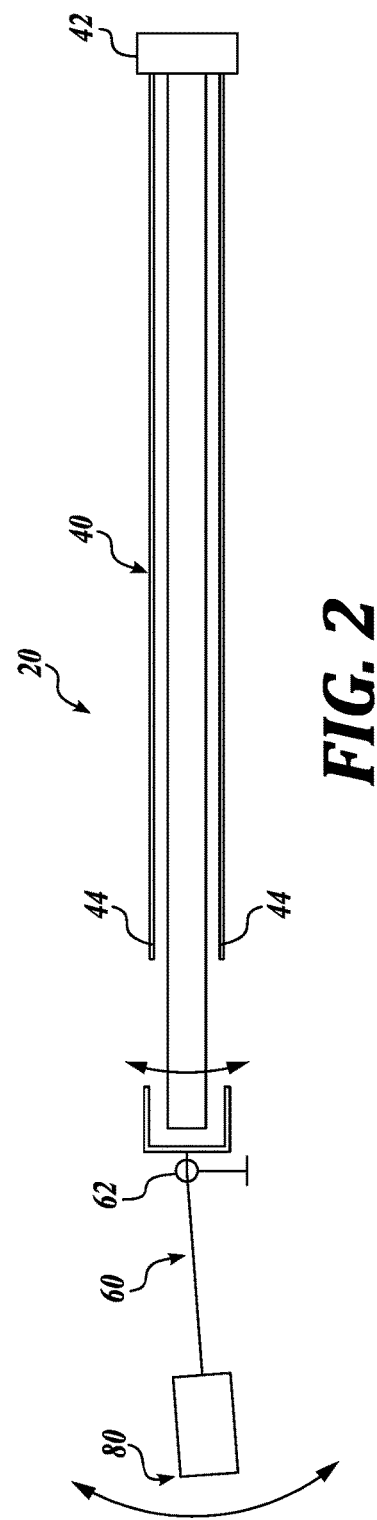
FIG. 1
FIG. 2

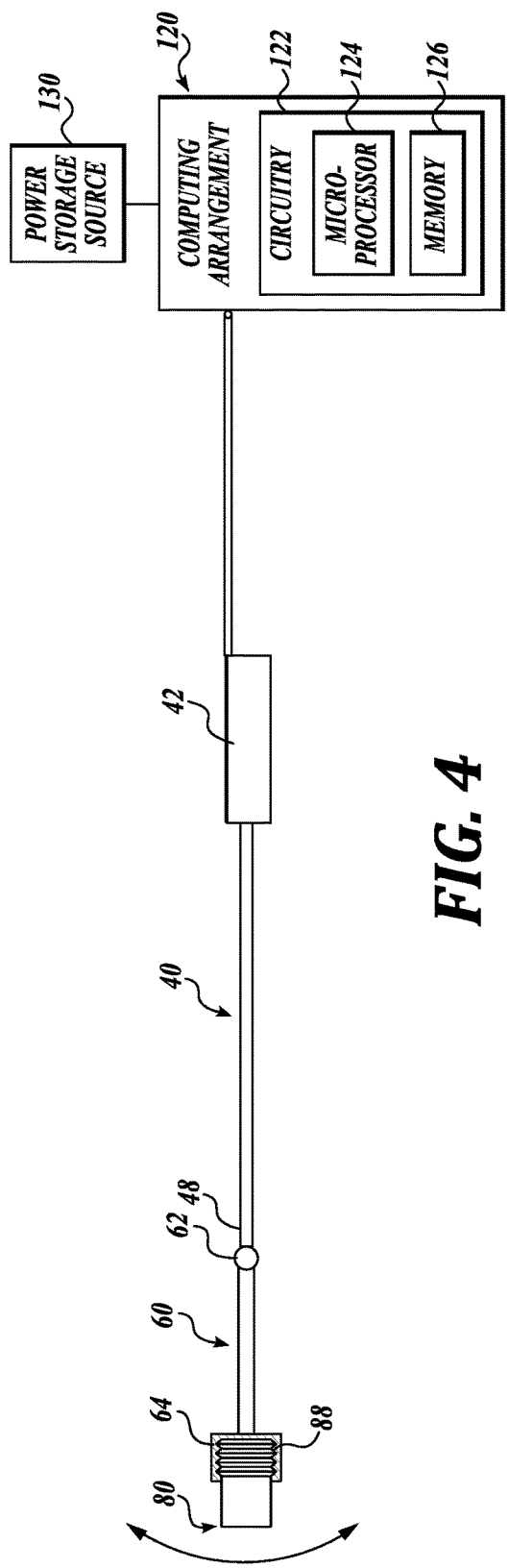
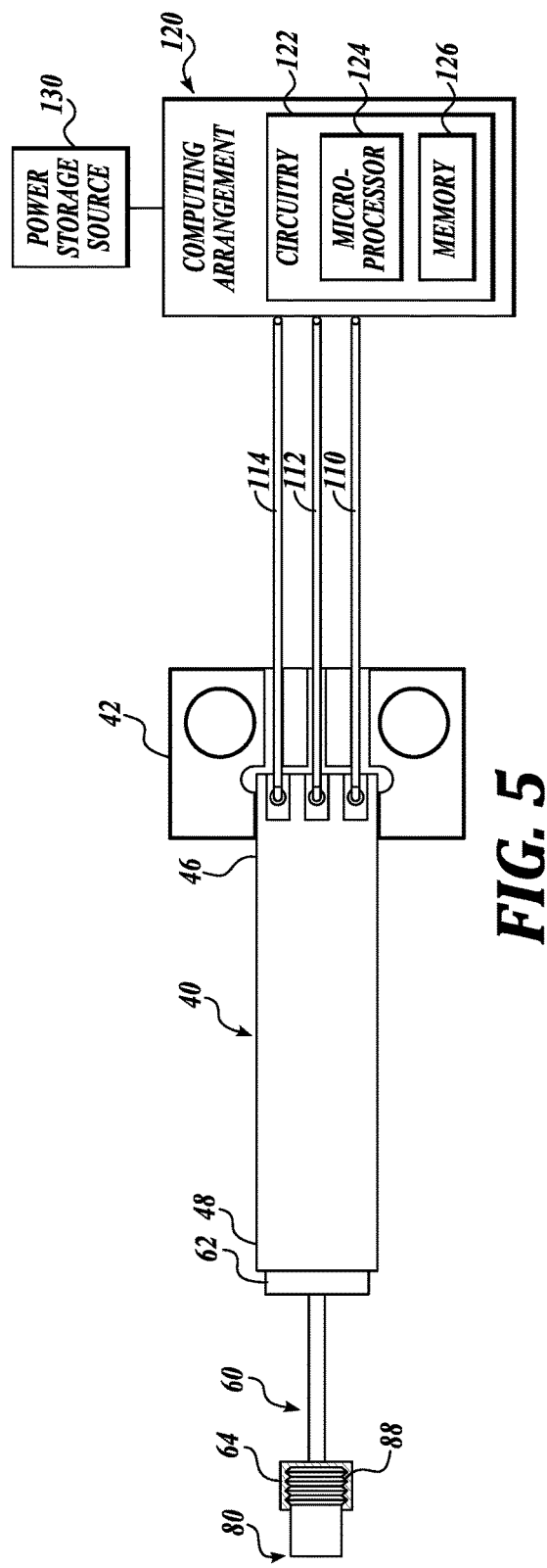
FIG. 4
FIG. 5

PIEZOELECTRIC SYSTEMS AND APPLIANCES FOR REMOVING EYE MAKEUP AND RELATED METHODS

SUMMARY

Examples of the present disclosure seek to address problems associated with removing makeup, particularly eye makeup applied to a periorbital region of a body. In this regard, examples described herein relate to a system including an applicator removably coupled, directly or indirectly, to a piezoelectric beam and configured to oscillate the applicator and remove makeup from a portion of a body. The systems described herein are, thus, configured to remove makeup and avoid infecting or otherwise damaging, for example, an eye.

In one aspect, the present disclosure provides a system generally including an applicator removably coupled with a lever, a piezoelectric beam rotatably coupled to the lever opposite the applicator, fixed at an end opposite the lever, and operably coupled to a power source, and circuitry configured to oscillate a portion of the piezoelectric beam and the applicator.

In another aspect, the present disclosure provides a system generally including a piezoelectric beam fixed at a first end region and operably coupled to a power source, a lever rotatably coupled to a second end region of the piezoelectric beam opposite the first end region, an applicator configured to be removably coupled with the lever opposite the second end region of the piezoelectric beam; and circuitry configured to oscillate a portion of the piezoelectric beam and the applicator.

In accordance with any of the embodiments disclosed herein, the lever is configured to amplify the oscillation of the applicator relative to the oscillation of the portion of the piezoelectric beam.

In accordance with any of the embodiments disclosed herein, the system includes a sheath configured to limit the oscillation of the portion of the piezoelectric beam.

In accordance with any of the embodiments disclosed herein, the circuitry is further configured to oscillate the portion of the piezoelectric beam and the applicator at a frequency that does not include a resonant frequency of an ocular cavity.

In accordance with any of the embodiments disclosed herein, the circuitry is further configured to provide a haptic feedback after a treatment period.

In accordance with any of the embodiments disclosed herein, the circuitry is further configured to provide a haptic feedback when the applicator is loaded beyond a limit.

In accordance with any of the embodiments disclosed herein, the system a reservoir carrying a cleansing fluid, wherein the reservoir is coupled to the piezoelectric beam and configured to expel the cleansing fluid with the oscillation of the portion the piezoelectric beam.

In accordance with any of the embodiments disclosed herein, the applicator resists bio-contamination.

In accordance with any of the embodiments disclosed herein, the applicator is configured to oscillate at a rate and for a duration that avoids scratching a cornea.

In accordance with any of the embodiments disclosed herein, the applicator is configured to carry a cleansing solution.

In accordance with any of the embodiments disclosed herein, the piezoelectric beam is a bimorph piezoelectric beam.

In accordance with any of the embodiments disclosed herein, the applicator is one of a plurality of applicators configured to removably couple with the lever opposite the second end region of the piezoelectric beam.

In accordance with any of the embodiments disclosed herein, the plurality of applicators is individually carried in packaging.

In accordance with any of the embodiments disclosed herein, the applicator is carried in a cleansing solution.

In accordance with any of the embodiments disclosed herein, the applicator is carried in a sterile package.

In accordance with any of the embodiments disclosed herein, the system includes a reservoir configured to removably couple with the piezoelectric beam, wherein the reservoir carries a cleansing solution.

In another aspect, the present disclosure provides a method of cleaning a periorbital region generally including contacting an applicator with the periorbital region and oscillating the applicator by applying an oscillating voltage to a piezoelectric beam coupled with the applicator.

In accordance with any of the embodiments disclosed herein, the method includes amplifying the oscillation of the applicator relative to an oscillation of the piezoelectric beam with a lever, rotatably coupled to the piezoelectric beam at a first end region and removably coupled with the applicator at a second end region.

In accordance with any of the embodiments disclosed herein, the method includes expelling a cleansing solution from a reservoir coupled to the piezoelectric beam, wherein the reservoir is compressed by an oscillation of the piezoelectric beam.

The above summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of claimed subject matter will become more readily appreciated as the same become better understood by reference to the following detailed description, when taken in conjunction with the accompanying drawings, wherein:

FIG. 1 is a side view of a system in accordance with an aspect of the disclosure;

FIG. 2 is a side view of another system in accordance with an aspect of the disclosure;

FIG. 4 is a side view of a schematic illustration of a system in accordance with an aspect of the disclosure;

FIG. 5 is a top view of a schematic illustration of a system in accordance with an aspect of the disclosure;

DETAILED DESCRIPTION

Figure 3A:
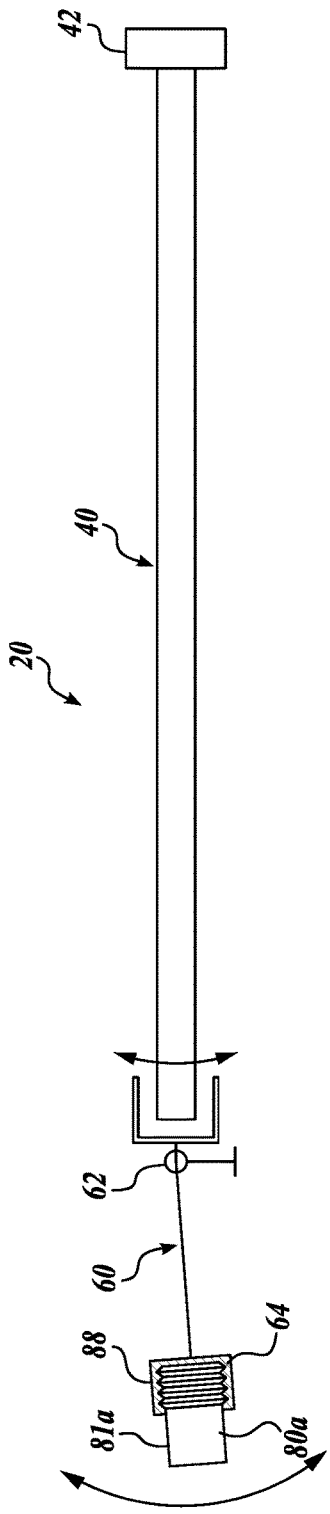
FIG. 3A is a side view of another system in accordance with an aspect of the disclosure.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The present disclosure relates generally to handheld personal care appliances, systems, and methods. Generally described, personal care appliances typically include an end effector or applicator for cleaning or otherwise treating a portion of skin or other portion of a body in order to produce desired functional results. Examples of such appliances include powered cleansers, such as a powered brush.

Makeup, particularly eye makeup, is often persistent when applied to a portion of skin and frequently requires a cleansing solution and agitation to remove. However, the periorbital region of a body, to which eye makeup is frequently applied, presents particular challenges to makeup removal. The periorbital region of a body and surrounding areas are sensitive; eyelid skin is thin and fragile. Further, eyes can be easily infected with bacteria from the application of a dirty cleansing device. Additionally, the eye itself may be easily damaged, for example, by scratching a cornea. Furthermore, with respect to resonant electromechanical personal care appliances, an ocular cavity has a resonant frequency and application of a resonant force at or near this resonant frequency of an ocular cavity may damage or dislocate an eye.

To that end, the following discussion provides examples of systems that include an applicator removably coupled to a piezoelectric beam. As will be described in more detail below, the piezoelectric beam is configured to oscillate, which in turn, oscillates the applicator. In that regard, and as will be described in more detail below, the piezoelectric beam is configured to oscillate the applicator in a manner safe and effective for removing makeup, such as eye makeup, applied to a periorbital region of a body.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

FIG. 1 illustrates a representative system 20, shown here as a personal handheld appliance, including a piezoelectric beam 40 and an applicator 80. In an embodiment, the applicator 80 is configured for application to and cleaning of a periorbital region. Non-limiting examples of applicator 80 materials include chemical resistant materials, elastic material allowing compression and expansion of the applicator element, elastomers (e.g., PVC, PU, EVA, Nitrile, Silicone, Butyl, SIS, SEBS, EPDM, etc.), ethylene propylene diene rubbers, flexible elastomeric thermo-compressed foam optionally covered with a textile c materials, fluorosilicones, natural or synthetic sponge materials, polymers, rubber, and the like.

In an embodiment, at least a portion of the applicator 80 comprises one or more sponge forming materials. In an embodiment, at least a portion of the applicator 80 comprises one or more elastomeric materials. In an embodiment, at least a portion of the applicator 80 comprises one or more polymeric materials. In an embodiment, at least a portion of the applicator 80 comprises silicone. In an embodiment, at least a portion of the applicator 80 is formed from a material having a Shore 00 hardness ranging from 00 to 40. In an embodiment, at least a portion of the applicator 80 is formed from a material having a Shore 00 hardness ranging from 00 to 30. For example, in an embodiment, at least a portion of the applicator 80 is formed from super soft silicone having a Shore 00 hardness ranging from 00 to 30.

As shown, a lever 60 interconnects the piezoelectric beam 40 and the applicator 80. In this regard, the piezoelectric beam 40 is rotatably coupled to the lever 60 opposite the applicator 80. Additionally, as shown, the end of the piezoelectric beam 40 opposite the lever 60 is fixed at an end 42. In this regard and as will be described in more detail below, the piezoelectric beam 40 is configured to oscillate the applicator 80 when the piezoelectric beam is operably coupled to an oscillating power source (not shown).

The piezoelectric beam 40 includes one or more piezoelectric materials configured to exhibit a piezoelectric effect wherein the one or more piezoelectric materials deform in response to an accumulation of electric charge therein. Such piezoelectric materials include any piezoelectric materials suitable to oscillate at a frequency. Suitable piezoelectric materials include, for example, piezoelectric crystals, piezoelectric polymers, piezoelectric semiconductors, and the like.

In an embodiment, the lever 60 is rotatably coupled to the piezoelectric beam 40. In an embodiment, the lever 60 includes a hinge 62, configured to facilitate rotation of the lever 60 relative to the piezoelectric beam 40. In this regard, the lever 60 is configured to amplify the oscillation of the applicator 80 relative to the oscillation of a portion of the piezoelectric beam 40 not fixed at the end 42. As a portion of the piezoelectric beam 40 oscillates, the lever 60 is free to rotate beyond the limits of the oscillation of that oscillating portion of the piezoelectric beam 40, thereby also amplifying the oscillation the applicator 80.

Still referring to FIG. 1, the system 20 in an embodiment includes a reservoir 100 carrying, containing or otherwise associated with a cleansing fluid 106. As shown, the reservoir 100 is fixed against movement and is positioned with respect to the piezoelectric beam 40 such that movement of the piezoelectric beam 40 causes the reservoir 100 to expel the cleansing fluid 106. In an embodiment, the reservoir 100 is coupled to the piezoelectric beam 40 by a coupler 108 that physically transmits forces generated by the oscillation of the piezoelectric beam 40 to the reservoir 100. In an embodiment, the reservoir 100 is compressed by the oscillation of the piezoelectric beam 40 and the coupler 108, thereby expelling a portion of the cleansing fluid 106.

In an embodiment, the reservoir 100 is removably coupleable to the system 20. In this regard, the reservoir 100 can be replaced when, for example, the cleansing fluid 106 has been completely expelled from the reservoir 100.

In an embodiment, the system 20, including the reservoir 100 and associated cleansing fluid 106, is configured to expel the cleansing fluid 106 on a portion of the applicator 80. In this regard, the reservoir 100 in one embodiment includes a spout 104 in fluid contact with the cleansing fluid 106 and is configured to expel the cleansing fluid 106 on a portion of the applicator 80. As a result, the system 20 is configured to provide the cleansing fluid 106 to the applicator 80 and, when the applicator 80 is applied to a periorbital region of a body, assist in cleaning the periorbital region.

In an embodiment, the system 20 includes a piezoelectric beam 40, at least a portion of which is configured to oscillate when an oscillating voltage is applied to the piezoelectric beam 40. However, in some embodiments, piezoelectric materials employed may be brittle and could break when deformed past a particular displacement. In that regard, attention is now turned to FIG. 2, where another representative embodiment of the system 20, including piezoelectric beam 40 is illustrated. As shown, the system 20 in this embodiment includes a sheath 44 configured to limit the oscillation displacement of the piezoelectric beam 40. In an embodiment the sheath 44 surrounds at least a portion of the piezoelectric beam 40 and, thereby, limits its oscillation. In an embodiment, the piezoelectric beam 40 oscillates in a plane and portions of the sheath 44 flank the piezoelectric beam 40 in the oscillation plane, thereby limiting the oscillation of the piezoelectric beam 40. In an embodiment, the sheath 44 is coupled to the end 42 and extends along a portion of the length of the piezoelectric beam 40. In an embodiment, the sheath 44 extends along substantially the entire length of the piezoelectric beam 40.

In an embodiment, the system 20 is configured to displace the applicator 80 during oscillation in a range of between about 15 millimeters to about 1 micron. In an embodiment, the system 20 is configured to displace the applicator 80 during oscillation in a range of between about 10 millimeters and about 5 microns. In an embodiment, the system 20 is configured to displace the applicator 80 during oscillation in a range of between about 5 millimeters and about 1 millimeter. In an embodiment, the system 20 is configured to displace the applicator 80 during oscillation in a range of between about 100 microns and 50 microns.

The piezoelectric beam 40 can have any length suitable for oscillating the applicator at an appropriate frequency and with a suitable displacement for cleaning a periorbital region of a body. In an embodiment, the piezoelectric beam 40 has a length of between about 10 cm and about 1 cm. In an embodiment, the piezoelectric beam 40 has a length of between about 5 cm and about 1 cm. In an embodiment, the piezoelectric beam 40 has a length of between about 4 cm and about 2 cm.

In an embodiment, the system 20 includes electronics for controlling one or more operations of the system 20. In that regard, attention is directed to FIG. 4, where a representative embodiment of a system 20, in accordance with the present aspect, is schematically illustrated. In the embodiment shown, the electronics include a computing arrangement 120, and a power storage source 130, such as a rechargeable battery, operably coupled to the computing arrangement 120. The computing arrangement 120, in some embodiments, includes circuitry, such as a microprocessor 124 and memory 126, that is configured and arranged to control the operation of the piezoelectric beam 40. In some embodiments, the memory 126 includes one or more programs, which, for example, when executed by the microprocessor 124 causes the piezoelectric beam 40 to be operated according to a treatment regimen or protocol, for example, by applying an oscillating voltage to the piezoelectric beam thereby oscillating a portion of the piezoelectric beam and the applicator 80.

In an embodiment, the circuitry 122 is further configured to oscillate the portion of the piezoelectric beam 40 and the applicator 80 at a frequency that does not include the resonant frequency of an ocular cavity. In this regard, the system 20 is configured to avoid damaging an ocular cavity and/or an eye contained therein during operation of the system 20.

In an embodiment, the system 20 is configured to oscillate the applicator 80 at sub-sonic frequency. In an embodiment, the system 20 is configured to oscillate the applicator at a frequency between about 20 Hz and about 1 Hz. In an embodiment, the system 20 is configured to oscillate the applicator 80 at a sonic frequency. In an embodiment, the system 20 is configured to oscillate the applicator at a frequency between about 200 Hz and about 20 Hz. In this regard, the system 20 is configured to oscillate the applicator at a frequency that mimics a natural rubbing frequency.

In an embodiment, the circuitry 122 is further configured to provide a haptic feedback after a treatment period. In this regard, the system 20 is configured to, for example, provide a signal to a user when a suggested treatment period for a first eye is complete and suggesting to a user to begin cleansing or otherwise treating a second eye.

In an embodiment, the circuitry 122 is further configured to provide a haptic feedback when the applicator 80 is loaded beyond a limit. In this regard, the system 20 is configured to provide a signal designed to alert a user when the applicator 80 is loaded past a recommended limit, which could, for example, damage or break the piezoelectric beam 40 or damage a periorbital region. In an embodiment, the circuitry 122 is configured to provide a haptic feedback when the applicator 80 is loaded beyond a limit of between about 50 g to about 150 g.

Figure 6:
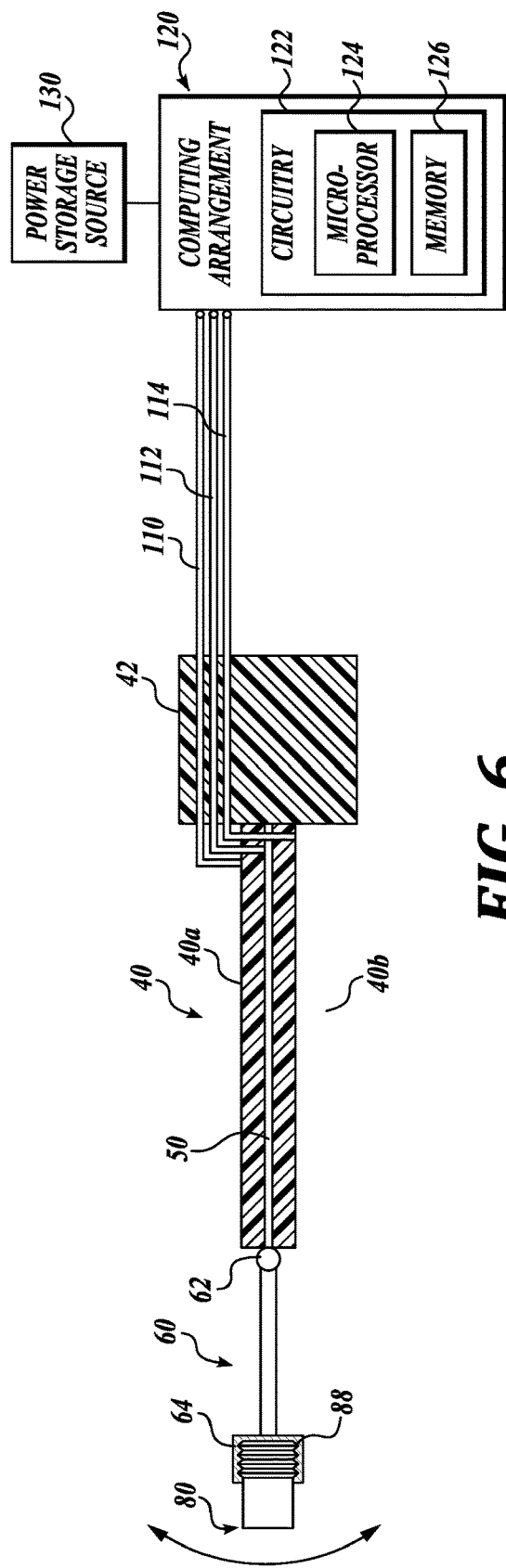
FIG. 6 is a side view of a schematic illustration of the system of FIG. 5 in partial cross section.

In an embodiment, the piezoelectric beam 40 is a bimorph piezoelectric beam. In that regard attention is directed to FIGS. 5 and 6, where there are shown representative embodiments of a system 20, in accordance with the present aspect, including a bimorph piezoelectric beam 40. The bimorph piezoelectric beam 40 in some embodiments includes a first piezoelectric element 40a conductively coupled on a first side to a conductive portion 50. Additionally, the bimorph piezoelectric element includes a second piezoelectric element 40b coupled to a second side of the conductive portion 50.

In an embodiment, the bimorph piezoelectric beam 40 is operably coupled to the computing arrangement through a number of leads 110, 112, 114. In this regard, the system 20 is configured to operate according to a number of drive modes.

In an embodiment, the system 20 is configured to operate in a single-side voltage control mode in which, for example, a positive voltage is applied between lead 114 and lead 112, thereby accumulating charge in the first piezoelectric element 40a and displacing a portion of the bimorph piezoelectric beam 40 in a first direction. Likewise, in accordance with another embodiment of a single-side voltage control mode, a negative voltage is applied between lead 110 and lead 112, thereby accumulating charge in the second piezoelectric element 40b and displacing a portion of the bimorph piezoelectric beam 40 in a second direction. In certain embodiments, a varying voltage is applied to the bimorph piezoelectric beam 40 configured to oscillate at least a portion of the bimorph piezoelectric beam 40.

In an embodiment, the system 20 is configured to operate in a differential voltage control mode, in which the bimorph piezoelectric beam 40 can be controlled both in a first direction and a second direction. In the differential voltage control mode, circuitry 122 is configured to provide differential voltages to, for example, leads 114 and 110. A varying voltage is applied to, for example, lead 112. For example, 7.5 V is applied to lead 114 and −7.5 V is applied to lead 110.

A voltage varying between, for example, 7.5 V and −7.5 V is applied to lead 112. In this regard, the system 20 is configured to displace the bimorph piezoelectric beam 40 in the first direction and second direction. The differential voltage control mode is configured to oscillate a portion of the piezoelectric beam with a displacement similar to a single-side voltage control mode but at about half the maximum applied voltage and, accordingly, about half the displacement of the piezoelectric beam 40 in a particular direction. Such a drive mode, therefore, introduces less strain on the piezoelectric beam 40 than a single-side voltage control mode for a given applicator 80 displacement and, may be preferable in certain embodiments.

As above, in an embodiment, circuitry 122 is configured to provide a varying voltage to the piezoelectric beam 40. In an embodiment, the varying voltage is a periodically-varying voltage, configured to oscillate the piezoelectric beam 40 in a periodic fashion. The periodically-varying voltage may be any periodically-varying voltage suitable to oscillate the piezoelectric beam 40. In an embodiment, the periodically-varying voltage varies sinusoidally. In an embodiment, the periodically-varying voltage is a square wave.

Figure 3B:
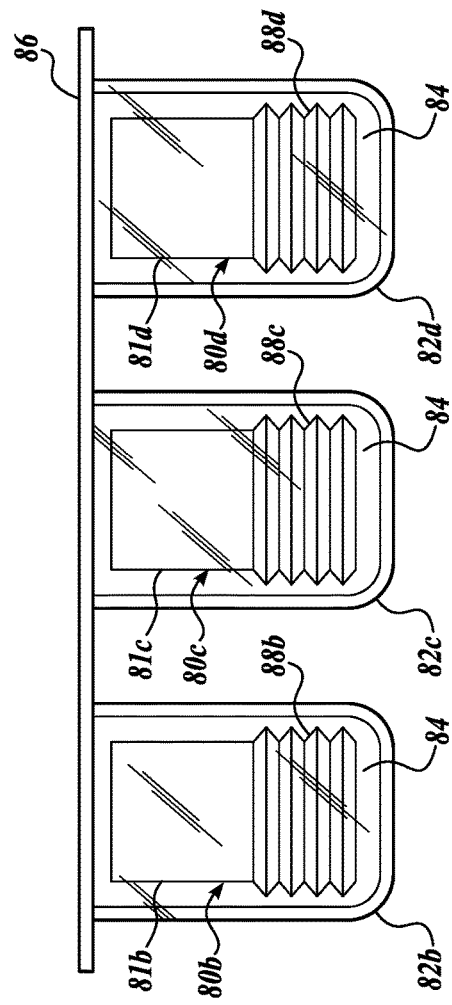
FIG. 3B is a side view of applicators coupleable to a system in accordance with an aspect of the disclosure, the applicators carried by packaging.

In an embodiment, the applicator 80 is configured to be removably coupled to the lever 60, and thus, can be replaced with another applicator 80. In that regard, attention is directed to FIGS. 3A and 3B, in which representative embodiments of a system 20 including a plurality of applicators 80*a-d* are illustrated. As shown, applicator 80*a* is removably coupled to lever 60. In an embodiment, applicator 80 is removably coupled to the system 20 through a coupler 64. In an embodiment, the applicator 80 includes, for example, threads 88 configured to cooperatively couple with threads carried by the coupler 64. In an embodiment, the one or more of the applicator 80 and the coupler include an adhesive (not shown). In an embodiment, the applicator 80 and the coupler 64 include hook and loop closures (not shown).

In this regard, the applicator 80*a* is configured to be uncoupled from the system 20 and replaced when, for example, applicator 80*a* is soiled, saturated with makeup, or otherwise unsuitable to clean a periorbital region of a body.

In an embodiment, one or more of the plurality of applicators 80*a*-80*d* are individually carried in packaging 86. In this regard, a user can selectively open portions of the packaging 86 individually carrying one or more of the plurality of applicators 80*b*-80*d* and remove one or more of the plurality of applicators 80*b*-80*d* for use. As shown, in an embodiment, each of the plurality of applicators 80*a*-80*d* includes threads 88*a*-88*d* and an application portion 81*a*-81*d*, configured to contact a periorbital region of a body.

As described elsewhere herein, the applicator 80 is suitable for cleaning a periorbital region on an eye. In this regard, in an embodiment, the applicator 80 is configured not to scratch a cornea of an eye. Accordingly, in an embodiment, the applicator has a durometer lower than that of a cornea of an eye.

In an embodiment, the applicator 80 includes an application portion 81 including a material suitable for cleaning a periorbital region. In an embodiment, the applicator 80 includes a porous material, such as a sponge, configured to absorb a cleansing fluid 106. In an embodiment, the applicator 80 includes a material chosen from a woven material, a non-woven material, natural fibers, synthetic fibers, and the like suitable for cleaning a periorbital region of a body.

Figure 7B:
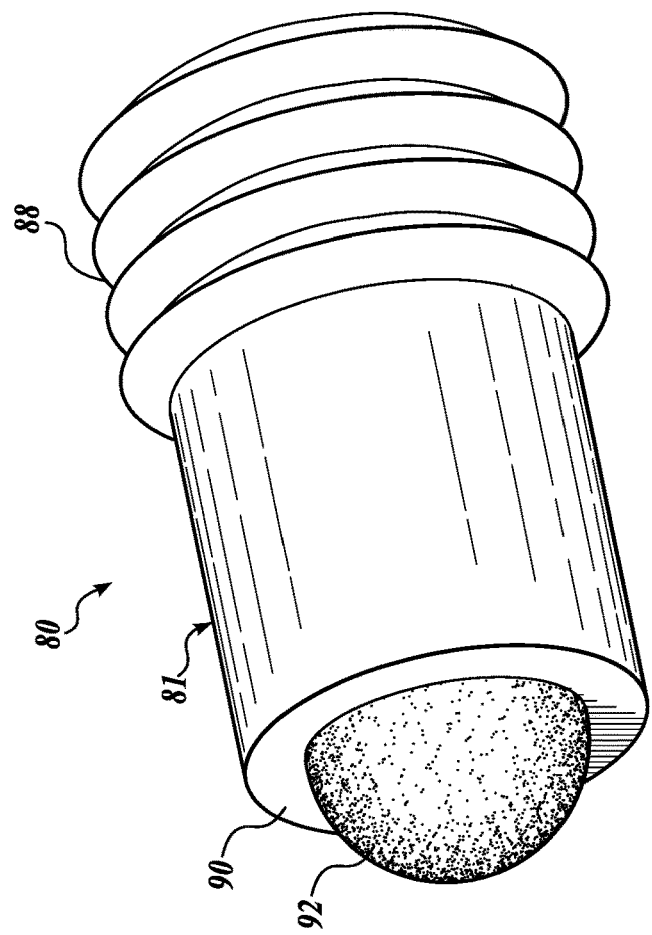
FIG. 7B is a perspective view of the applicator of FIG. 7A.
Figure 7A:
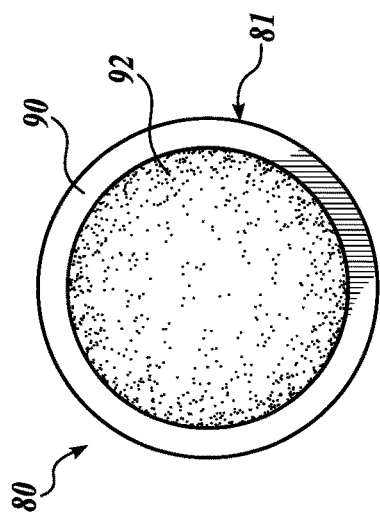
FIG. 7A is front view of an applicator in accordance with an aspect of the disclosure.

The applicator 80 in some embodiments includes a number of portions having varying densities and different durometers. In that regard, attention is directed to FIGS. 7A and 7B, where representative embodiments of an applicator 80, in accordance with the present aspect, are illustrated. As shown in accordance with certain embodiments herein, the applicator 80 includes an application portion 81 including a first portion 92 having a relatively-low first durometer and being configured to contact a portion of a periorbital region of a body including an eyelid. In an embodiment, the first portion 92 has a durometer lower than the durometer of a cornea. Additionally, in an embodiment, the applicator 80 includes a second portion 90 concentrically surrounding the first region 92, wherein the second portion has a second durometer higher than the first durometer. In this regard, the applicator 80 is configured to clean portions of a periorbital region that may be covered in makeup without scratching or otherwise damaging a cornea.

In an embodiment, the applicator 80 is carried in a cleansing solution 84 suitable, for example, for cleansing a periorbital region of a body. In an embodiment, the applicator 80 is carried in a sterile package 86. In this regard, the system 20 including packaging is suitable to clean a periorbital region in a way that avoids or limits the risk of infecting an eye.

In another aspect, the present disclosure provides a method of cleaning a periorbital region of a body. In an embodiment, the method includes contacting an applicator with the periorbital region; and oscillating the applicator by applying an oscillating voltage to a piezoelectric beam coupled with the applicator. In an embodiment, the method includes contacting the periorbital region with a system 20, including applicator 80, described elsewhere herein. As above, by applying an oscillating voltage to a piezoelectric beam, such as piezoelectric beam 40, the piezoelectric beam and applicator oscillate according to the applied oscillating voltage.

In an embodiment, the method includes amplifying the oscillation of the applicator relative to an oscillation of the piezoelectric beam, for example piezoelectric beam 40, with a lever 60, rotatably coupled to the piezoelectric beam at a first end region and removably coupled with the applicator at a second end region. As described elsewhere herein, by amplifying the oscillation of the applicator, for example, applicator 80, relative to an oscillation of the piezoelectric beam, stress on the piezoelectric beam can be reduced through lower piezoelectric beam displacement.

In an embodiment, the method includes expelling a cleansing solution from a reservoir coupled to the piezoelectric beam. In an embodiment, the cleansing solution is expelled from the reservoir and onto at least a portion of the applicator. In an embodiment, the cleansing solution is expelled from the reservoir and onto at least a portion of the periorbital region. As above, in an embodiment, the reservoir, for example reservoir 106, is compressed by an oscillation of the piezoelectric beam, for example piezoelectric beam 40, through a coupler, such as coupler 108, thereby expelling the cleansing fluid 106.

Certain embodiments disclosed herein utilize circuitry in order to implement treatment protocols, operably couple two or more components, generate information, determine operation conditions, control an appliance or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, circuitry of the system 20 includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operably coupled to at least one computing device to control (electrical, electro-mechanical, software-implemented, firmware-implemented, or other control, or combinations thereof) at least one parameter associated with the application of cyclical movement by the system 20, for example, controlling the duration and peak cyclic or oscillation frequency of the end effector of the system 20.

In an embodiment, circuitry of the system 20 includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A system comprising:
    an applicator removably coupled with a lever;
    a piezoelectric beam rotatably coupled to the lever opposite the applicator, fixed at an end opposite the lever, and operably coupled to a power source; and
    circuitry configured to oscillate a portion of the piezoelectric beam and the applicator.

2. The system of claim 1, wherein the lever is configured to amplify the oscillation of the applicator relative to the oscillation of the portion of the piezoelectric beam.

3. The system of claim 1, further comprising a sheath configured to limit the oscillation of the portion of the piezoelectric beam.

4. The system of claim 1, wherein the circuitry is further configured to oscillate the portion of the piezoelectric beam and the applicator at a frequency that does not include a resonant frequency of an ocular cavity.

5. The system of claim 1, wherein the circuitry is further configured to provide a haptic feedback after a treatment period.

6. The system of claim 1, wherein the circuitry is further configured to provide a haptic feedback when the applicator is loaded beyond a limit.

7. The system of claim 1, further including a reservoir carrying a cleansing fluid, wherein the reservoir is coupled to the piezoelectric beam and configured to expel the cleansing fluid with the oscillation of the portion the piezoelectric beam.

8. The system of claim 1, wherein the applicator resists bio-contamination.

9. The system of claim 1, wherein the applicator is configured not to scratch a cornea.

10. The system of claim 1, wherein the applicator is configured to carry a cleansing solution.

11. The system of claim 1, wherein the piezoelectric beam is a bimorph piezoelectric beam.

12. A system comprising:
  a piezoelectric beam fixed at a first end region and operably coupled to a power source;
  a lever rotatably coupled to a second end region of the piezoelectric beam opposite the first end region;
  an applicator configured to removably couple with the lever opposite the second end region of the piezoelectric beam; and
  circuitry configured to oscillate a portion of the piezoelectric beam and the applicator.

13. The system of claim 12, wherein the applicator is one of a plurality of applicators configured to removably couple with the lever opposite the second end region of the piezoelectric beam.

14. The system of claim 13, wherein the plurality of applicators is individually carried in packaging.

15. The system of claim 12, wherein the applicator is carried in a cleansing solution.

16. The system of claim 12, wherein the applicator is carried in a sterile package.

17. The system of claim 12, further including a reservoir configured to removably couple with the piezoelectric beam, wherein the reservoir carries a cleansing solution.

\* \* \* \* \*